United States Patent [19]

Leveen et al.

[11] Patent Number: 4,840,939
[45] Date of Patent: * Jun. 20, 1989

[54] TREATMENT OF CANCER WITH PHLORIZIN AND ITS DERIVATIVES

[76] Inventors: Harry H. Leveen, 321 Confederate Cir., Charleston, S.C. 29407; Robert F. Leveen, 312 Lombard St., Philadelphia, Pa. 19147; Eric G. Leveen, 141 S. Battery, Charleston, S.C. 29401

[ * ] Notice: The portion of the term of this patent subsequent to Aug. 4, 2004 has been disclaimed.

[21] Appl. No.: 27,413

[22] Filed: Mar. 18, 1987

Related U.S. Application Data

[63] Continuation-in-part of Ser. No. 640,170, Aug. 13, 1984, Pat. No. 4,684,627, which is a continuation-in-part of Ser. No. 300,136, Sep. 8, 1981, abandoned.

[51] Int. Cl.$^4$ .......................... A61K 37/02; C07H 1/00
[52] U.S. Cl. ....................................... 514/25; 530/370; 530/395; 536/4.1; 536/18.1; 536/18.2
[58] Field of Search .................. 514/25; 530/370, 395; 536/4.1, 18.1, 18.2

[56] References Cited

U.S. PATENT DOCUMENTS 3,523,937  8/1970  Biegeleisen ...................... 536/18.4
4,684,627  8/1987  Leveen et al. ...................... 514/25

OTHER PUBLICATIONS

Warburg, The Metabolism of Tumors, Richard R. Smith & Co., N.Y. 1931.
Warburg, Science, 123:3191, Feb. 24, 1956.
Biochemica et Biophysica Acta, 591:209, 1980.
J. Nat. Can. Inst., 62:3, Jan., 1979.
Cancer Res., 40:1699, 1980.
Cancer Res., 39:1968, 1979.
Cancer Res., 33:66, 1974.
Cancer Res., 29:391, Feb., 1969.
Cancer Res. 37:2336, 1977.
Cancer, 47:2026, 1981.
SA Med J., 59:518, 1981.
Ann NY Acad Sci, 72:103, 1980.
Science, 235:1492, Mar. 20, 1987.
J. Neurochem, 29:959, 1977.
Can. Res., 41:1165, 1981.
J. Nat. Can. Ins. 66:497, 1981.
Can. Res., 39:4242, Oct. 1979.
J. Physol 169:229, 1963.
Science, 235:1495, Mar. 20, 1987.
Harvey Lectures, 56:63, 1961.
J. Clin Invest., 12:1083, 1933.
J. Clin Invest., 13:749, 1934.
Nutri Reviews, 33:23, 1975.
Radiol. 113:209, 1974.
Radiol. 117:447, 1975.
Biochem. and Biophysica. Res. Comm. 82:787, 1978.
Cancer Res., 36:1035, 1976.
Proc. Soc. for Experimental Biology & Medicine, vol. 11, pp. 1913–1914, Benedict & Lewis.
Proc. Soc. for Experimental Biology & Medicine, vol. 11, p. 135, Wood & McLean.
Kolber et al., Chem. Abst., vol. 67, 1967, p 115099(q).
Ilinich et al., Chem. Abst., vol. 73, 1970, p 129240(q).
Nature, No. 4019, p. 663, Nov. 9, 1946.
Nature, vol. 159, p. 100, Jan. 18, 1947.
Woodcock, Chem. Abst., vol. 41, 1947, P 2859.
J. Bio. Chem., vol. 218, No. 9, p. 4978, 1972.
Physiol. Review 7, 1927, p. 385.
Physiol. Review 25, 1945, p. 255.
Z. Natureforch 36c, p. 255, 1981.
Zemplen et al., Chem Abst., vol. 36, 1942, p. 6163.
Leschbe, Chem. Abst., 1910, p. 2506.

Primary Examiner—John Kight
Assistant Examiner—Nathan M. Nutter
Attorney, Agent, or Firm—John S. Hale

[57] ABSTRACT

Malignant, neoplastic cells are treated by inhibiting glucose transport into the cell by administering phlorizin, phloretin or its analogs while concurrently administering adjunct therapy such as heat, radiation or chemotherapy. In this manner, the cells are prevented from growing or repairing the damage caused by the adjunct therapy, which can be administered in dosages that would otherwise be non-lethal if used alone.

26 Claims, No Drawings

TREATMENT OF CANCER WITH PHLORIZIN AND ITS DERIVATIVES

CROSS-REFERENCE TO RELATED APPLICATIONS

This application is a continuation-in-part of application Ser. No. 640,170 filed Aug. 13, 1984 and now U.S. Pat. No. 4,684,627 which is a continuation-in-part of application Ser. No. 300,136 filed Sept. 8, 1981 and now abandoned.

SUMMARY OF THE INVENTION

The present invention relates to a method and composition for inhibiting glucose transport across cell membranes, and more specifically to a method by which the growth of malignant neoplastic cells can be halted and such cells kept from repairing and rejuvenating themselves. The invention is particularly concerned with a combined treatment whereby malignant cells are made more susceptible to lethal damage from exposure to otherwise non-lethal doses of energy and anti-tumor agents.

BACKGROUND OF THE INVENTION

Researchers have long sought for a biochemical difference by which malignant cells could be distinguished from normal cells. The work of Warurg in the early part of the twentieth century (Warburg, *The Metabolism of Tumors*, Richard R. Smith & Co., New York, 1931) focused attention on the differences in the way that cancer cells metabolize glucose. Using a concept advanced by Pasteur, Warburg considered that cancer cells ferment while normal cells respire. The arguments advanced by Warburg (Annual Review of Biochemistry. 33:1, 1964) seemed to characterize the majority of rapidly growing malignant cells, and the occasional instance where the metabolism of the tumor does not strictly fit Warburg's criteria is limited to very slow growing cancers which do not produce death by cachexia and widespread metastasis.

However, some recent, knowledge with respect to the regulation of the energy metabolism in the cell was unknown to Warburg. For instance, the Crabtree effect (inhibition of respiration by glycolysis) is observed in practically all cells (Biochema et Biophysica Acta 591:209, 1980). The addition of glucose to anaerobic suspensions of glucose starved malignant cells causes a burst of respiration and glycolysis with lactate production which results in an inhibition of both respiration and glycolysis to values below those observed prior to the addition of glucose.

The rate limiting factor in glucose metabolism which determines the quantity of lactate formed in the cell has been shown to be dependent upon the rate at which glucose is transported across the cell membrane. This knowledge suggests that the biochemical defect in cancer cells does not reside in fermentation or respiration; but, rather, the primary defect must be the increased rate of glucose transport across the cell membrane. This must be related either to an enhancement of the transport mechanism or an actual increase in the receptor sites for glucose transport which are present in the membrane of the cell wall; and there is excellent substantiation for the latter explanation that a greater number of receptor sites are responsible.

The rate of glucose transport across cells has been shown to be directly related to the growth potential of the cell. Glucose is a requirement for energy needs related to synthesis, as well as for actual structural requirements in the synthesis of macromolecules (J Nat Can Inst. 62:3, January 1979). Because malignant cells exhibit an extensive augmentation of glucose transport, they are understandably much more sensitive to drugs which inhibit glucose transport than are normal cells. The magnitude of abnormal carbohydrate metabolism of malignant cells increases the competition for glucose which develops between rapidly growing tumors and the host's normal cells. Warburg mentions that the glycolysis of tumor cells can be so rapid as to reduce the blood sugar in diabetic patients. For example, the blood sugar concentration in rats with a rapidly growing sarcoma remains normal until the tumor/body weight ratio increases above 0.15. At ratios of 0.31 or greater, hypoglycemia occurs. Liver glycogen declines at high tumor/body weight ratios. Gluconeogenesis from lactate increases thirty fold over autogenous gluconeogenesis from endogenous alanine (Cancer Res. 40:1699, 1980). Similar findings have been made in patients with rapidly progressive malignant disease (Cancer Res. 39:1968, 1979; Cancer 33:66, 974). Obviously, cancers sequestrate glucose and glucose utilization in cancer patients is extremely high. The high potential for the malignant tumor to metabolize glucose has even caused it to be referred to as a glucose trap (Acta Chir Scan [Suppl] 498:141, 1980).

This excessive glucose turnover in malignant patients has again focused attention on the role of glucose metabolism in cancer cachexia. One consequence of the anaerobic metabolism of glucose is the release of lactate into the circulating blood. The lactic acid is transported to the liver by the circulating blood. The liver converts the lactic acid to glucose thus completing the Cori cycle. The conversion of lactate to glucose is energy consuming and has been estimated to account for 10% increase in energy expenditure (Cancer Res. 37:2336, 1977). The production of lactate may be so excessive in patients with cancer that with impairment of liver physiology as with extensive liver metastasis, lactic acidosis may occur (Cancer 47:2026, 1981). The severe carbohydrate drain causes excessive gluconeogenesis which further depletes the cancer patient (SA Med J. 59:518, 1981)(Ann NY Acad Sci, 72:103, 1980).

Glycogen synthesized from glucose is abundantly stored in cancer cells (Cancer 19:98, 1966); however, the glycogen content decreases during the exponential phase of tissue growth. Brain tumors for example contain five times as much glycogen as small mammal brains (J. Neurochem. 29:959, 1977). This further supports the concept that increased glucose transport is a significant requirement for the rapidly growing cancer cell. Slower growing tumors contain more glycogen than more rapidly growing tumors which utilize the glucose more swiftly (Can. Res. 41:1165, 1981). These factors support the concept that cancer cells transfer glucose more swiftly than do normal cells.

These energy related revelations have also turned attention to the glucose metabolism of growing cancer cells as a mechanism for the control of cancer growth. Lonidamine has been found to be a selective inhibitor of aerobic glycolysis in urine tumor cells (J Nat Can Ins. 66:497, 1981). Dactylirin is a new antibiotic which has a potential anticancer effect since it influences the energy yielding carbohydrate mechanisms which function in malignant cells (Can Res. 39:4242, October 1979).

DESCRIPTION OF THE INVENTION

In accordance with the present invention a process and compositions are provided for treating malignant neoplasms such as cancers and sarcomas in mammals by inhibiting glucose entry into the malignant cell to thereby render the cell more susceptible to the injurious effect of chemotherapy, radiation, heat or anoxia and prevent repair or growth of the cell. Glucose entry into the malignant cell is inhibited by administering effective amounts of phlorizin, its glucuronide, 4-deoxyphloretin-2-D-glucoside, phloretin or cytochalasin B or a combination of these compounds either alone or in combination with Lonidamine or other chemotherapeutic agents such as bleomycin or mitomycin C. Phloretin is the aglucone portion of the phlorezin molecule and also inhibits glucose transport across the cells. Different tissue differ in their responsiveness to phloretin as compared to phlorezin. For instance, phlorezin is much more effective at blocking transfer across the kidney tubules and intestinal mucosa than is phloretin. On the other hand, phloretin is much more effective in blocking transfer of glucose across red blood cells. It has been postulated that phloretin blocks non sodium dependent glucose transport more effectively than does phlorezin. Glucose transport across renal tubular cells and intestinal mucosa is sodium dependent. If sodium transport is blocked, glucose transport will not be inhibited by phlorezin. Many tissues exhibit both type of receptors. For instance, there are both sodium dependent and non sodium dependent transfer sites in the capillary endothelium of the blood brain barrier. In tissues with such mixed type of receptors. Phlorezin and phloretin are mutually competitive for the receptor sites. Both compounds will inhibit glucose transport but it takes a higher concentration of phlorizin in non sodium dependent transfer sites. Because of its low toxcity and the fact that phlorizin is more water soluble it has been the drug of choice in spite of the fact that for some transfer sites phloretin may be more active. This has also caused the does of phlorezin to sometimes be raised beyond the dosage indicating a complete block of glucose transfer in the kidneys. Work on phloretin indicates that more water soluble derivatives of phloretin are possible without the loss of pharmacological activity.

These compounds are especially effective in preventing glucose transport across malignant cell membranes, thereby suppressing the growth of cancer especially when used in conjunction with chemotherapy, radiation, heat or other techniques. The pharmaceutical composition according to the invention comprises phlorizin, its glucuronide, cytochalasin-B or 4-deoxyphloretin-2-D-glucose, preferably together with a pharmaceutically acceptable carrier. These compositions may be solid or liquid and can be used in forms currently used in medicine such as tablets, capsules, syrups and injectable preparations. Because of its poor absorption, the compositions of the invention is preferably administered parenterally, dissolved in a suitable carrier such as ½ normal saline. Orally acceptable carriers are those currently used in medicine such as calcium carbonate, starch, lactose, talc, magnesium stearate, gum acacia, aqueous alcohol, glycol or oil solutions or suspensions.

While sufficient phlorizin or its analogs should be given to saturate glucose binding sites in the tumor cells, excess dosage is simply excreted in the urine.

The dosage required to effectively inhibit cancer growth is easily determined since the patient acts as his own bioassay. The concentration which makes the tumor cells impermeable to glucose, makes other normal cells in the body also impermeable to glucose. The extent to which glucose transfer has been blocked can be assessed by measuring the concentration of glucose in the urine. Urine is formed by glomerular filtration. The glomerular filtrate contains all the constituents of blood except protein. As the glomerular filtrate passes down the renal tubules, the proximal tubule reabsorbs glucose. Therefore, normal urine contains no glucose unless there is some impairment of reabsorption or the blood concentration of glucose exceeds the renal tubules ability to reabsorb glucose as occurs in diabetes mellitus. When the dosage is adequate to prevent glucose entry into cells, the proximal tubular cells can no longer absorb glucose and glucosuria occurs. When total blocking of glucose absorption into the cell occurs, glucose then appears in the urine in almost the same concentration that it is present in the serum depending on the degree of water absorption of the urine. The correct dosage of the composition of the invention can be determined by measuring the glucose clearance, which approaches 125 cc's per minute and which is the same as the xylose and inulin clearance. The creatinine clearance is a good substitute since it is only slightly higher than the inulin clearance.

Clinical experience has shown that, the composition of the invention is preferably administered in a continuous drip, approximately 1 mg per kilo of body weight per hour as a maintenance dose after total phlorization to completely abolish glucose entry into cells. An initial loading dose of 4–6 mg per kilo of body weight is usually desirable to completely phlorizinize a patient as evidenced by the failure of the tubular cells to absorb glucose. This can be given by a slow push or over a ten minute interval. The duration of the effects last approximately one to one and one-half hours when administered intravenously as a single dose. With oral therapy, much of the dose appears in the stool. That glucose reabsorption in the kidney is completely blocked can be determined by comparing clearance of glucose to the clearance of xylose after administration.

Xylose clearance is determine by taking the concentration of xylose in the blood and measuring the total amount of xylose excreted in a time period divided by the plasma concentration and the number of minutes of collection. This will determine how many cc's of blood were completely cleared of xylose every minute. Xylose is a non-metabolized sugar which is not reabsorbed by the renal tubules. When glucose entry into cells is completely blocked, glucose clearance and xylose clearance are almost the same. Other substances can be used in place of xlyose such as inulin or sorbitol.

The glucose clearance approaches 125 cc's per minute when the patient is completely phlorozinized. This is easily obtained by measuring the quantity of glucose excreted, divided by the serum glucose concentration and the number of minutes over which the urine was collected. Urinary and serum glucose concentrations can approach one another but the concentration in the urine is always higher unless water reabsorption from the tubules is minimal which can occur at high glucose concentrations since osmotic diuresis occurs and the tubules are unable to do osmotic work. When the glucose clearance is identical to a substance that is filtered by the glomerulus but not secreted or reabsorbed by the tubules (such as inulin or xylose), glucose utilization is completely blocked.

Generally, it has been found that the administration of a total dosage of about 200-1000 mg of phlorizin or the indicated derivative per kilogram of body weight is an adequate dose in most patients. One need not fear giving an excessive quantity of phlorizin, however, since this substance has proven to be non-toxic and is rapidly excreted in the urine. The effect of phlorizin is dependent on a critical concentration in the extracellular fluid which will completely block all of the receptors sites for glucose.

The composition is generally administered during intervals of chemotherapy or radiation therapy by heating, radiation or chemotherapeutic drugs. Heat therapy can be administered by radiofrequency thermotherapy. Complete phlorizination for twenty-four hours prior to therapy reduces cellular glycogen levels and renders the therapy more effective. This dose is sufficient to reduce the blood glucose concentration to low levels and to partly or completely deplete cellular glucose. Further inhibition of glucose entry into the cancer cell is extended to the time of patient therapy by heat, chemotherapy or radiation and continued for 24 hours post therapy. The patient should be carefully observed for salt depletion. If for any reason it is necessary to interrupt the therapy, it can be counteracted with glucose infusions.

Although not required for effective treatment in accordance with this invention, the effectiveness of phlorizin or its indicated derivatives or analogs can be enchanced by the inclusion of a chemotherapeutic agent such as lonidamine, bleomycin or mytomycin in amounts of 50 to 500 mgs per kilo of body weight.

For I.V. infusion of phlorizin ten grams of phlorizin or the indicated analogs are dissolved in 20 cc's of 95% ethyl alcohol which is then mixed with 930 cc's of warm or hot 0.5 normal sodium chloride solution to which one ampule of sodium bicarbonate (50 mq in 50 ml $H_2O$) has been added. This mixture may require heating until it is warm enough to fully dissolve the phlorizin. After initial administering of the loading dose, the infusion is slowed to 10-15 cc per hour depending on body weight.

While not wishing to be bound to a particular theory, it has been postulated that phlorizin and phloretin and their indicated analogs and derivatives act on cells by attachment of the glucosyl unit to the glucose binding sites in the transfer site while the phloretin group has a high affinity for a cellular binding site adjacent the entrance of the glucose site. The aglucone unit attaches to the sites with great affinity while glucose occupies the enzyme site (J Physol. 169:229, 1963). Phlorizin is easily disassociated from the receptor site and its effect on glucose transport is not lasting. Also, since it is a competitive inhibitor of glucose, high concentrations of glucose tend to displace phlorizin from the binding site. The aglucone portion of the molecule attaches to the surface of the cell and exerts its action on the cell surface rather than in the interior of the cell (Harvey Lectures 59:53, 1961).

Insulin and glucose enhance transport of glucose across the cell membrane. Their administration produce an increased concentration of glycogen in muscle tissues such as the diaphragm. This increases in glycogen stimulated by insulin and glucose can be prevented by the in vitro or in vivo administration of phlorizin (Harvey Lectures 56:63, 1961). This is strong evidence that phlorizin prevents glucose entry into the cells. Blocking the entry into the renal tubular cell leads to glucosuria in phlorizinized animals and humans. The action of phlorizin on the excretion of glucose in humans is identical to the action of phlorizin on the excretion of glucose in other lower animals (J Clin Invest. 12:1083, 1933). Phlorizin is relatively non-toxic and has been administered to man parenterally and by mouth in wafer form. Doses as high as 15 grams have been administered in a single oral dose (J Clin Invest. 13:749, 1934). It has been given intravenously and subcutaneously to humans. Phlorizin by inhibiting glucose entry into the renal tubular cell causes glycosuria but since it also inhibits glucose entry into intestinal mucosal cells, absorption from the intestines is inhibited and sugar may be present in the feces.

In accordance with the present invention, studies have been directed toward the in vivo observation of the effect of large dosages of phlorizin, 5-thio-d-glucose and lonidamine both by themselves and in combination with each other in Erlich carcinoma transplanted to the back of Swiss mice. These tumors were observed with drug therapy in the above combination with and without localized hyperthermia developed by radiofrequency dielectric heating of the localized tumor sites. Tumor temperatures were measured during therapy for varying periods of time. Temperatures from 39° to 44° were achieved in the tumors as measured by thermocouples placed into the center of the tumor. In addition, animals were treated for two days and then sacrificed. The tumors were then excised for histology. Phlorizin alone enhanced the ability of otherwise non-lethal dosages of heat to produce tumor necrosis and the addition of lonidamine and other chemotherapeutic agents slightly increased the effect further. Phlorizin with heat is very destructive and it is unnecessary to achieve the high lethal temperatures to kill carcinoma in animals when used without phlorizin. The tumor destruction was complete with low temperatures in the lonidamine plus phlorizin treated animals. Animals treated with phlorizin alone also showed extensive to complete necrosis with heat applied by radiofrequency thermotherapy. Necrosis of normal tissue was not seen on microscopic section in spite of the fact that tumor tissue intimately infiltrating normal muscle tissue was found to be completely destroyed.

Phlorizin is useful by itself and in combination with other agents affecting carbohydrate metabolism since it deprives the tumor cell of primary energy source. This effect is accentuated by temperature elevation. 5-thio-glucose was not found to enhance the effect of phlorizin on tissue necrosis with heat or by itself. This is explained by the fact that phlorizin blocks glucose entry into the cell and similarly blocks the entrance of thio-glucose into the cell allowing thio-glucose to be completely spilled into the urine. When radioactive gold thio-glucose is administered to growing mice, the gold thio-glucose is concentrated in the satiation center of the brain and animals become obese. The destruction of this center renders the mice hyperphagic (Am J Physio. 226:574, 1974). When phlorizin is administered to these animals, glucose transport is inhibited thus preventing a lethal collection of gold-thio-glucose to concentrate in the region of the hypothalmus. Therefore, phlorizin protects by preventing the entrance of gold thio-glucose into the hypothalmic cells (Nutri Reviews 33:23, 1975).

In addition to animal tests, tests have also been performed on tumor cells (mastoma) growing in vitro.

When glucose absorption was blocked, cell growth in tissue culture was completely suppressed.

The survival of cells heat-treated in the absence of nutrients is greatly reduced compared to those heat treated with nutrients and the ability of cells to repair heat damage is impaired. The state of the cell cycle also depends on nutriment supply and oxygen availability. The center of a cancer contains only cells in the synthetic phase, while the hyperemic edge of cancerous tissue exhibits rapid growth and good viability. Cells in the central plateau phase are more susceptible to thermal destruction than are the cells in the proliferative phase (Radiol. 113:207, 1974). Hypoxic cells are also more susceptible to heat which again implicates the role of metabolism in ameliorating cell destruction y heat. (Radiol. 117:477, 1975).

Glucose is essential for DNA synthesis through the pentose phosphate pathway (SA Med J, p. 518, April 4, 1981). Since ribose-5-phosphate is essential for DNA and RNA synthesis, any damage to DNA caused by radiation and chemotherapy cannot be repaired if glucose entry into the cell is prevented. Increased glucose transport occurs in cancer cells because their anaerobic metabolism is less effective than aerobic metabolism. Malignant cells are totally dependent on glucose since malignant cells deprived of glucose are unable to maintain their ATP levels for periods longer than four hours whereas normal cells have no difficulty in maintaining their ATP levels in the absence of glucose (Biochem et Biophysica Res Comm. 82:787, 1978). The repair of hyperthermic damage is totally dependent on metabolic processes in which the metabolism of glucose plays an important role. The lethal thermal damage to malignant cells caused by two one-hour heating periods at 44° C. has been quantitated.

Heating is most lethal when no interval between the one hour heating periods is allowed. If the interval between the heatings is greater than four hours (bringing the temperature back to 37° C. between heatings), additional killing over and above that which occurs with a single heating is not observed since the thermal damage is completely repaired by the metabolic processes of the cell during the four hour interval between heatings. Nonetheless, if the temperature between heatings is dropped to 0° C. instead of 37°, repair of thermal damage is prevented and the killing is identical to a steady two hour heating. This demonstrates the strong role of metabolism in repairing thermal damage (Cancer Res. 36:1035, 1976).

Chemotherapy and radiation damage to cells is characterized by single and double breaks in the DNA chain. The repair of this damage is also a metabolic process (Radio. 123:475, 1977) requiring the metabolism of glucose.

Phlorizin, and equivalents by prohibiting glucose entry into the interior of the cell, impairs the vitality, metabolism, and repair and injury to cells caused by outside forces and changes sublethal cellular damage to lethal damage thus enhancing the effect of chemotherapy, radiation and heat.

The following examples further illustrate and support the clinical efficacy of the present invention:

EXAMPLE 1

A thin female 57 years of age entered with sarcoma of duodenum resected 3 years prior. Patient was jaundiced and work up indicated obstruction of common bile duct. Tumor was debulked around porta hepatis and cholecystojejunostomy was done. Patient was then given life time dose of radiation and chemotherapy. Pathology report of patient was a leiomyosarcoma. About one year later, the tumor recurred in the umbilical area requiring further debulking at which time large portion of abdominal mass was resected.

Further debulking was done from the abdominal wall, transverse colon and hepatic region. The tumor was not possible to completely resect at any surgery and each time the lesion was more extensive. The patient again became jaundiced and another laparotomy with debulking was performed. A T-tube was placed in the common duct and a gastroenterostomy was performed.

The patient was treated with antibiotics for cholangitis and infection of abdominal wall wound. She was then started on phlorizin given continuously for 12-24 hours with local heat. Systemic temperature rose to 40° C. Vinblastin and Mitomycin C were given I.V. in very small doses. The entire tumor mass became necrotic. Massive necrosis of necrotic tumor became liquified and infected and have required multiple drainages with catheters placed by radiographers under x-ray control. Bowel wall which was replaced by nectrotic tumor tissue has communicated with a large intraabdominal abcess which has been drained. Sepsis is now being controlled. CT scans show multiple areas of tumor liquification and cavitation. The patient's survival with large necrotic masses is questionable but patient is being supported and sepsis seems under control.

EXAMPLE 2

A 51 year old female had a low anterior resection for cancer of rectum. At time of surgery, hepatic metastases were discovered. Had full course of radiation to pelvis, post surgery. She was treated with 5 FU, Mitomycin C and Novotrome without response. Was starated on 8-12 hour phlorizin plus the same chemotherapeutic agents. Made an immediate response with regression of tumor and no further bowel obstruction.

EXAMPLE 3

A 57 year old male had a melanoma over right scapula removed. There was a local recurrence and a local infection with paraincisional melanosis. This was removed with lymph nodes. Pathological diagnoses was Clark level two melanoma. 7 years later, a cerebral recurrence was found. There were two lesions in frontal lobes and one in parietal area. Was treated with radiation without response. All therapy was then abandoned and the patient was told he had 60 days to live.

The patient was started on small doses of Vincrestine, methyl CCNU and received phlorizin by bolus 5 grams and mild heat to head by RFTT. There was a 50% reduction of lesion by NMR scan. NMR scan of brain was negative. He had a recurrance and was treated but chemotherapy omitted. The lesion did not respond and patient died.

EXAMPLE 4

46 year old female developed a melanoma of the right leg during pregnancy. An excision of primary with lymph node desection and removal was done. Pathology reported that lymph nodes were positive for melanoma. Metastases appeared in head and lungs. Patient was placed on Vincristine and Precarbizone. Severe pain in abdomen probably caused by hemorrhage into a liver mets. She was treated with a bolus of 5 grams o±phlorizin and decadron to lower any possible inflamatory response from necrotic tumor tissue along with RFTT of 50 watts to head and the chemotherapy which had previously been unsuccessful. Vincristine Methyl CCNU and procarbozine was restarted in small doses. The lesion in her brain completely resolved on CT scan. The liver and abdominal diseases had increased and patient died in June of liver and abdominal disease without any recurrance in the head.

EXAMPLE 5

38 year old female developed a melanoma of left axilla which was widely excised with adjacent lymph nodes. Lymph nodes were negative for metastases. She developed plural effusion with multiple nodules in left lung. Received 50.0 mg 5 F.U. and 5 mg. mitomycin C intraplurally. Heated with 100 watts R.F.T.T.. Given vincrestine procarbozine CCNU but did not respond. Chest was drained again in September. Received same treatment plus phlorizin over 12 hours. Responded and now is tumor free for past 11 months.

EXAMPLE 6

A 39 year old woman presented with total obstruction from stomach and a large bowel fistula from previous surgery. She was unable to take any food by mouth. She underwent treatment with R.F.T.T. to area of obstruction after 8 hours of continuous phlorizin infusion. Small doses of chemotherapy were also administered I.V. Patient responded with disappearance of complete gastric outlet obstruction. She is now on full diet and the Fistula has spontaneously closed.

EXAMPLE 7

Patient had carcinoma of breast and previous mastectomy but experienced a large recurrence in the axilla. Because of a generalized vasculitis poorly understood she did not receive chemotherapy but only received phlorizin and heat treatment. She was given a bolus containing 2.5 grams of phlorizin and 75 watts of R.F.T.T. to axilla. Lesion dried up and CT scan was negative.

EXAMPLE 8

34 year old male had a resection of sigmoid and descending colon for cancer of colon. Pathological report described perivascular invasion, lymph node invasion and diffuse periotoneal seeding. All lymph nodes could no be removed. Was treated with 5FU Mitomycin and a bolus of phlorizin. Now has normal CT scan of liver and abdomen. C.E.A. 2.8 and has remained tumor free for 1 year.

EXAMPLE 9

54 year old female with cancer of breast amputated and was placed on chemotherapy and tomoxifen and local radiation. There was a metastases to the 4th ventricle of the brain on CT scan. Patient told no treatment possible and was sent to a terminal cancer hospital.

Was treated with mild heat, phlorizin and decadron without chemotherapy. CT scan now negative and patient remains well.

EXAMPLE 10

62 year old executive had adenocarcinoma of lung with metastases to brain. Three separate lesions appeared in brain on CT and NMR scans. Brain was radiated without response. Lung also radiated without response. Patient was started on 5FU mytomycin and phlorizin. CEA was 8.2. Scan has improved and only 1 small lesion is now visable in brain and 2 have disappeared. Lung lesion has disappeared. No other soft tissue metastases.

EXAMPLE 11

Primary tumor in colon was resected. Patient underwent liver resection for right hepatic metastatic colon cancer. No other tumor seen. Developed recurrent bowel obstruction and peritoneal seeding. Repeated bowel obstructions respond each time to chemotherapy and phlorizin. Laparotomy with a colostomy slowed massive tumor regression. Has improved long term survival.

EXAMPLE 12

56 year old man had cancer of rectum resected. Recurrance three years later in abdomen was treated with a bolus, heat mitromycin and 5FU. Patient developed renal shut down from obstructed ureters. There were liver metastases and abdominal tumor present. Patient was given 8–12 hour phlorizin plus chemotherapy as above and has responded with tumor regression and ureter is no longer obstructed.

EXAMPLE 13

78 year old female had anterior resection for cancer of rectum. She developed a recurrance one year later with radiation to pelvis. No response occured and the bowel was obstructed so a laparotomy was done and an end colostomy performed. Liver metastases were found. Laparotomy and exenteration was done for colovesical fistula. Biopsies were all positive for cancer post exenteration. Patient was treated with 8 hour infusion of phlorizin. Chemotherapy and heat were administered. All biopsies turned negative and there was no evidence of pelvic cancer. Pelvic biopsies were negative Liver metastases remain stable.

EXAMPLE 14

Nasopharangeal cancer treated by radiation and chemotherapy. Pathology was a poorly differentiated squamous cell carcinoma. Lesion spread to both sides of neck. Progressed on chemotherapy. Phlorizin was added by bolus to regime. Patient progressed very slowly. Eight hours of phlorizin was instituted with chemotherapy. Tumor regressed by 80%.

EXAMPLE 15

58 year old female had a right colon resection for carcinoma. The cancer had perforated the bowel wall and there was peritoneal seeding visable. All of the tumor could not be resected. CEA was 13.9 Was treated postoperatively with 5 FU Mitomycin C and phlorizin infusion plus mild heat. Last CT scan was negative for tumor and C.E.A. remains at low level of 3.0.

EXAMPLE 16

80 year old female with massive liposarcoma of left lower leg. Patient has had repeated resections of tumor mass of left lower leg. Patient was injected with mitomycin C and Vinblastin with phlorizin. Because of the shortage of phlorizin, it was injected intralesionally and a tourniquet applied to prevent reabsorption. The lesion has resolved with a 90% regression in tumor size. Requires occasional therapy with heat RFTT and chemotherapy but has not required further surgery.

EXAMPLE 17

48 year old female who had upper G.I. discomfort. She had been working with x-rays for 20 years. Exploratory laparotomy revealed cancer of stomach with diffuse metastases over peritoneum. The patient gradually deteriorated and developed partial bowel obstruction. She received 8-12 hours phlorizin infusion plus 5FU and mitomycin C and RFTT to area of obstruction. Obstruction resolved and went home to Texas. Returned 6 weeks later with another obstruction. Retreated. Mass reduced in size and obstruction overcome. Responds well to treatments.

EXAMPLE 18

54 year old obese female with metastases hypernephroma to brain, scalp and lungs. Primary tumor had been removed some years previously. Patient had failed chemotherapy and was dying. Phlorizin given in bolus of 2 grams with Lonidamine I.V. Heat given to head with conductive R.F.T.T. of 50-100 watts. Necrosis of tumor occurred immediately and patient went into acute cerebral edema requiring immediate neurosurgical decompression. The necrotic tumor was scooped out from brain. Pathology report confirmed that dead tumor tissue had caused acute edema. Tumor of scalp also became necrotic and disappeared leaving a scar biopsy free of tumor. CT scan now confirm that tumor in head had disappeared. Patient now alive and well.

EXAMPLE 19

37 year old male with massive liver cancer. The biopsies disclosed a carcinoid tumor but a search for the primary tumor did not disclose any intestinal primary. He was operated upon and the tumor proved to be completely unresectible. Patient was placed on high doses of chemotherapy both before and after surgery but it failed completely.

Patient had received phlorizin by bolus plus previously failed chemotherapy and lonidamine but responded only slowly. Therefore, he was switched to long term phlorizin over 12 to 24 hours with the same chemotherapy and heat regime and has responded to long infusions of phlorizin. The long infusion technique depleted the cell of glycogen and made it impossible for damage of cancer cell to be repaired. The results have been dramatic with marked response in weight gain, strength, well being. Tumor size has decreased significantly on direct palpation and CT scan. CT scan shows necroses of hepatic metastases.

The above noted examples represent numerous examples of treatment of patients with phlorizin taken from varours medical records showing patient treatment.

Having disclosed a preferred embodiment of the present invention, it is understood that changes may be made in the disclosed invention as set forth in the following claims.

What is claimed:

1. A method for inhibiting glucose transport into malignant neoplastic cells which comprises administering an effective amount of a compound or compounds selected from the group consisting of phlorizin, phloretin, phlorizin glucoronide, 4-deoxyphloretin-2-D-glucose, and cytochalasin-B to a human being.

2. The method of claim 1 wherein said compound or compounds are administered in combination with a chemotherapeutic agent selected from the group consisting of lonidamine, bleomycin and mytomycin.

3. A method for treatment of malignant neoplastic cells in a human being which comprises inhibiting glucose transport into said cells by administering to said human being an effective amount of a compound or compounds selected from the group consisting of phlorizin, phlorizin glucoronide, phloretin, 4-deoxyphloretin-2-D-glucose, and cytochalasin-B.

4. The method of claim 1 wherein said compound or compounds are administered in combination with a chemotherapeutic agent selected from the group consisting of lonidamine, bleomycin and mytomycin, 5-flurouricil, and cysplatinum.

5. The method of claim 1 wherein said compound or compounds is administered in a total amount of about 200 to 1000 mg per kilogram of body weight of said human being.

6. The method of claim 3 wherein said compound or compounds are administered in combination with a chemotherapeutic agent selected from the group consisting of lonidamine, bleomycin and mytomycin, 5-flurouricil, and cysplatinum.

7. The method of claim 6 wherein said compound or compounds is administered intravenously.

8. The method of claim 7 wherein said compound or compounds is administered initially as a dosage sufficient to block glucose transport into said cells followed by a continuous maintenance dosage.

9. The method of claim 8 wherein said initial dosage is about 4-6 mg per kilogram of body weight and said maintenance dose is administered at a rate of about 1 mg per hour per kilogram of body weight.

10. The method of claim 7 wherein said compound or compounds is administered intravenously from a saline solution of said compound or compounds.

11. The method of claim 3 wherein administering of said compound or compounds is done concurrently with subjecting said cells to additional therapy in the form of chemotherapy, thermal or radiation therapy.

12. The method of claim 11 wherein said compound or compounds is administered in combination with a chemotherapeutic agent selected from the group consisting of lonidamine, bleomycin and mytomycin.

13. The method of claim 11 wherein said compound or compounds is administered in a total amount of about 200 to 1000 mg per kilogram of body weight of said human being.

14. A method for treatment of malignant neoplastic cells in humans which comprises administering one or more compounds selected from the group consisting of phlorizin, phlorizin glucoronide, 4-deoxyphloretin-2-D-glucose in an amount effective to inhibit glucose transport in the cells along with one or more additional compounds selected from the group consisting of lonidamine, bleomycin and mytomycin while subjecting said cells to additional therapy in the form of chemotherapy, thermal or radiation therapy.

15. The method of claim 14 wherein the dosage of said one or more compounds is an effective amount of at least 200-1000 mg per kg of body weight and the dosage of said additional one or more compounds is 50 to 500 mg per kilo of body weight.

16. The method of claim 15 wherein said one or more compounds are administered intravenously concurrently with said additional therapy.

17. A method for treatment of neoplastic cells in humans which comprises administering phloretin in an effective amount to inhibit glucose transport in the cells while concurrently subjecting said cells to thermal treatment.

18. The method of claim 17 wherein said thermal treatment is at a dosage level that would otherwise be non-lethal if administered by itself.

19. The method of claim 17 wherein said phloretin is administered in combination with a chemotherapeutic agent selected from the group consisting of lonidamine, bleomycin and mytomycin, 5-flurouricil, and cis-platinum.

20. The method of claim 17 wherein said phloretin is administered in a total amount of about 200 to 1000 mg per kilogram of body weight of said human being.

21. The method of claim 17 wherein said phloretin is a compound administered intravenously.

22. The method of claim 21 wherein said compound is administered initially as a dosage sufficient to block glucose transport into said cells followed by a continuous maintenance dosage.

23. The method of claim 22 wherein said dosage is about 4–6 mg per kilogram of body weight and said maintenance dose is administered at a rate of about 1 mg per hour per kilogram of body weight.

24. The method of claim 21 wherein compound is administered intravenously from a saline solution of said compound.

25. A method for treatment of malignant neoplastic cells in humans which comprises administering one or more compounds which are effective to inhibit glucose transport in the cells while subjecting said cells to additional therapy in the form of chemotherapy, thermal or radiation therapy.

26. A method for treatment of malignant neoplastic cells in humans which comprises administering one or more compounds which are effective to inhibit glucose transport in the cells along with one or more additional therapeutically effective compounds while subjecting said cells to additional therapy in the form of chemotherapy, thermal or radiation therapy.

* * * * *